US010405825B2

(12) United States Patent
Rai et al.

(10) Patent No.: US 10,405,825 B2
(45) Date of Patent: *Sep. 10, 2019

(54) SYSTEM AND METHOD FOR AUTOMATICALLY DETERMINING CALIBRATION PARAMETERS OF A FLUOROSCOPE

(71) Applicant: Broncus Medical Inc., San Jose, CA (US)

(72) Inventors: Lav Rai, Sunnyvale, CA (US); Henky Wibowo, Cupertino, CA (US)

(73) Assignee: Broncus Medical Inc., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/639,756

(22) Filed: Jun. 30, 2017

(65) Prior Publication Data

US 2017/0296136 A1 Oct. 19, 2017

Related U.S. Application Data

(63) Continuation of application No. 14/234,183, filed as application No. PCT/US2012/047853 on Jul. 23, 2012, now Pat. No. 9,693,748.

(Continued)

(51) Int. Cl.
*A61B 6/08* (2006.01)
*G01D 18/00* (2006.01)
(Continued)

(52) U.S. Cl.
CPC ............... *A61B 6/582* (2013.01); *A61B 6/12* (2013.01); *A61B 6/485* (2013.01); *A61B 6/487* (2013.01);
(Continued)

(58) Field of Classification Search
CPC .. A61B 2017/00725; A61B 2034/2055; A61B 2090/363; A61B 2090/376; A61B 2090/3966; A61B 2090/3983; A61B 34/20; A61B 6/12; A61B 6/485; A61B 6/487; A61B 6/582; A61B 6/584; A61B 90/39; A61B 2018/2025; A61B 2090/3945; A61B 90/36; A61B 5/4504; A61B 5/4528; A61B 17/155; A61B 17/157; A61B 17/158; A61B 34/10; A61B 5/4514; A61B 2034/105; A61B 2034/108; A61B 17/154; A61B 17/1666; A61B 17/1675; A61B 17/1739; A61B 6/583; A61B 17/1668; A61B 6/032; A61B 2034/2072; A61B 2034/2068; A61B 2034/107; A61B 2090/364; A61B 5/06; A61B 6/547; A61B 90/10; A61B 6/4441;
(Continued)

(56) References Cited

U.S. PATENT DOCUMENTS 7,251,522 B2 * 7/2007 Essenreiter ............ A61B 34/20
600/424
8,374,678 B2 * 2/2013 Graumann ............... A61B 6/12
378/205

(Continued)

*Primary Examiner* — Irakli Kiknadze
(74) *Attorney, Agent, or Firm* — Richard Batt

(57) ABSTRACT

A method and system for estimating calibration parameters of a medical fluoroscope and more particularly a method and system which automatically determines intrinsic and distortion correction parameters of a fluoroscopy device.

18 Claims, 2 Drawing Sheets

Related U.S. Application Data

(60) Provisional application No. 61/511,028, filed on Jul. 23, 2011.

(51) Int. Cl.
  *A61B 6/00* (2006.01)
  *A61B 6/12* (2006.01)
  *A61B 34/20* (2016.01)
  *A61B 90/00* (2016.01)
  *A61B 17/00* (2006.01)

(52) U.S. Cl.
  CPC ............. *A61B 6/584* (2013.01); *A61B 34/20* (2016.02); *A61B 90/39* (2016.02); *A61B 2017/00725* (2013.01); *A61B 2034/2055* (2016.02); *A61B 2090/363* (2016.02); *A61B 2090/376* (2016.02); *A61B 2090/3966* (2016.02); *A61B 2090/3983* (2016.02)

(58) Field of Classification Search
  CPC .... A61B 17/1764; B82Y 30/00; G01N 23/04; G01N 2001/282; G01N 2035/00782; G01N 2035/00851; G01N 35/00732; G01N 2223/3035; G01N 23/046; G01N 23/083; G01B 15/02; G01B 21/042; G01B 3/30; A61N 5/1075; A61N 2005/1054; A61N 2005/1056; A61N 2005/1059; A61N 2005/1061; A61N 2005/1076; A61N 5/1045; A61N 5/1049; A61N 5/1065
  USPC .................................. 378/207, 205; 382/294
  See application file for complete search history.

(56) References Cited

U.S. PATENT DOCUMENTS

| | | | |
|---|---|---|---|
| 8,838,199 B2* | 9/2014 | Simon | A61B 6/481 378/165 |
| 8,845,191 B2* | 9/2014 | Ngar | A61N 5/1075 378/18 |
| 8,934,961 B2* | 1/2015 | Lakin | A61B 5/064 600/426 |
| 9,532,848 B2* | 1/2017 | Amiot | A61B 90/36 |
| 2003/0012342 A1* | 1/2003 | Suhm | A61B 6/12 378/205 |
| 2003/0095638 A1* | 5/2003 | Sabczynski | A61B 6/583 378/207 |
| 2006/0050988 A1* | 3/2006 | Kraus | A61B 90/36 382/294 |

* cited by examiner

SYSTEM AND METHOD FOR AUTOMATICALLY DETERMINING CALIBRATION PARAMETERS OF A FLUOROSCOPE

CROSS-REFERENCE TO RELATED APPLICATIONS

This application is a continuation application of U.S. non-provisional patent application Ser. No. 14/234,183, filed Mar. 25, 2014, which is a national phase filing under 35 U.S.C. 371 of International Patent Application No. PCT/US2012/047853, filed Jul. 23, 2012, which claims the benefit of U.S. provisional patent application No. 61/511,028, filed Jul. 23, 2011, and is hereby incorporated by reference.

FIELD OF THE INVENTION

This invention generally relates to medical fluoroscopy calibration and more particularly this invention relates to a method, which automatically determines intrinsic and distortion correction parameters of a fluoroscopy device in multiple positions.

BACKGROUND OF THE INVENTION

Minimally invasive surgery is surgery performed with only a small incision or no incision at all and is typically performed with an endoscope, bronchoscope, laparoscope, or like instrument.

In a bronchoscopic procedure, for example, a bronchoscope is inserted through the nose or mouth of the patient, advanced through the trachea and into a desired airway. The surgery may then be performed through the working lumen of the bronchoscope. A light source and camera at the tip of the bronchoscope enables the physician to observe the airway wall in real time. A skilled physician can identify his location along the airway and navigate to the desired location along the airway wall.

It is often desirable, however, to supplement endoscopic visualization with radiological guidance (e.g., by taking real time X-ray images of the region with a fluoroscope). In certain procedures radiologic guidance is necessary.

In a transbronchial needle aspiration (TBNA) procedure, for example, a long flexible catheter comprising a needle at the tip is advanced through the working lumen of the bronchoscope to the target site. The needle is then advanced through the airway wall outside of view of the bronchoscope to aspirate a sample of tissue. It is highly desirable or necessary to have fluoroscopy or an alternative means to view and track the needle once it is outside of view of the bronchoscope.

Various tracking approaches are available. One approach is described in US Patent Publication No. 2003/0181809 to Hall et al. (hereinafter referred to as "the Hall Publication"). The Hall Publication describes a method of visualizing a surgical instrument that has been introduced into an area of examination within a patient, in particular a catheter that is used during a cardiological examination or treatment, comprising the following steps: using a 3D image data set of the area of examination and generating a 3D reconstructed image of the area of examination, taking at least one 2D X-ray image of the area of examination in which the instrument is visualized, registering the 3D reconstructed image relative to the 2D X-ray image, and visualizing the 3D reconstructed image and superimposing the 2D X-ray image over the 3D reconstructed image on a monitor.

Another approach to track the surgical devices with fluoroscopic visualization is described in international patent application serial number PCT/US12/37026, filed May 9, 2012.

The performance of such visualization and tracking approaches are dependent on the performance and accuracy of the fluoroscopic projection images. The fluoroscope must therefore be properly calibrated. Stated alternatively, an un-calibrated camera can introduce errors and thwart tracking and registration performance.

Calibration data may be obtained off-line and be calculated by acquiring multiple fluoroscopic images of radio-opaque markers to determine such data as the focal lengths and camera center of fluoroscopic camera, and a representation of the deformation pattern wherein a checkerboard pattern appears curved when viewed in the fluoroscope, and variation of these parameters as the fluoroscope is rotated throughout its range of motion. The calibration factors can be specific to each fluoroscope. Examples of calibrating techniques include those described in References 2-5, and 8, listed below. However, off-line measurement can be slow, inconvenient, and susceptible human error.

A method and system to more accurately, more conveniently, and more rapidly determine the calibration parameters is desired.

SUMMARY OF THE INVENTION

One embodiment of the present invention is a method for determining calibration parameters of a medical fluoroscopic device. The method comprises the steps of: a) providing a calibration device comprising at least one reference marker visible under fluoroscopy; b) determining the position of the calibration device with a tracking device and a plate tool rigidly connected to the calibration device, the plate tool being sensed by the tracking device; c) calculating a pose of the reference marker based on the position of the calibration device and the position of the fluoroscopic device; d) receiving a 2D image of the calibration device using the fluoroscopic device; and e) calculating at least one calibration parameter of the fluoroscopic device based on image information from the 2D image and the pose of the reference marker. The position of the fluoroscopic device can be based on sensing a position of the fluoroscopic device with the tracking device. The tracking device may be a depth sensing camera or another type of 3D sensor.

In another embodiment, the position of the plate tool is determined with the tracking device wherein the plate tool is not directly connected to the calibration device.

In another embodiment, a system for calibrating a medical fluoroscopic device comprises: a computer workstation; a tracking device; a calibration plate having at least one reference marker visible under the fluoroscopic device; and a plate tool in fixed engagement with the calibration device and comprising a plurality of locators visible with the tracking device. The processor being operable to calculate a pose of the reference marker based on the position of the calibration device and the position of the fluoroscopic device; to receive a 2D image of the calibration device using the fluoroscopic device; and to calculate at least one calibration parameter of the fluoroscopic device based on image information from the 2D image and the pose of the reference marker.

Examples of calibration parameters include pixel per MM, focal length, distortion, and pose of reference marker relative to fluoroscope.

In another embodiment, the plate tool comprises a plurality of arms each having a different length.

In another embodiment the calibration device is a planar circular shape. In another embodiment the calibration device comprises a plastic plate.

In another embodiment, the reference markers of the calibration plate are a plurality of metal beads.

In another embodiment, a calibration assembly comprises a calibration plate, a plurality of fixed reference markers visible under a fluoroscope or x-ray device, and a plate tool in a known rigidly fixed engagement to the calibration plate. In one embodiment the plate tool includes a plurality of infrared visible locators.

In one embodiment the plate is comprised of polymer and the reference markers include at least three metal beads.

The description, objects and advantages of the present invention will become apparent from the detailed description to follow, together with the accompanying drawings.

DETAILED DESCRIPTION OF THE INVENTION

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail).

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is to be appreciated that unless defined otherwise, all technical and scientific terms used herein have the same meaning as commonly understood by one of ordinary skill in the art to which this invention belongs.

Figure 1:
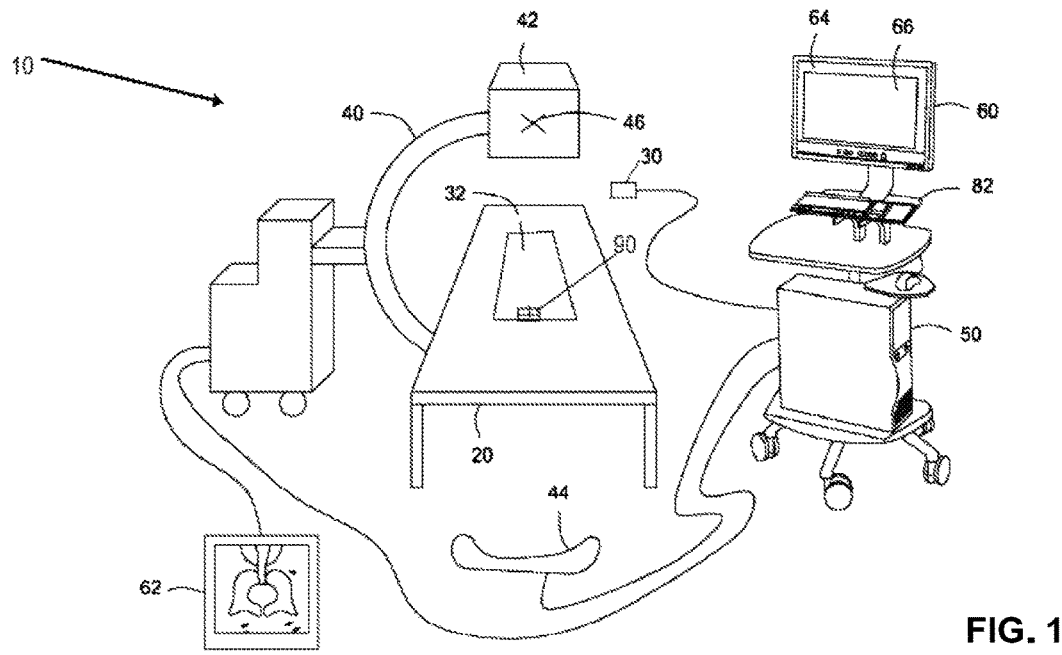
FIG. 1 is a schematic illustration of a calibration system and fluoroscopic device.

One embodiment of the invention is shown in FIG. 1. The system 10 in FIG. 1 shows a calibration device 32, a tracking device 44, and a fluoroscope unit 42. Each component is connected to workstation 50. The workstation includes a memory device, a programmed microprocessor, an input device such as a keyboard 82, and a display 50.

Fluoroscopy device 42 and tracker device 44 are shown in communication with the computer to deliver or receive information, instructions, or data. It is to be understood, however, that the invention is not limited to a particular type of workstation or computer. A wide range of computers having programmable components may be used to carry out the steps of the invention. An example of a workstation is a Dell Computer Model No. T5400, with Dual-core Intel Xeon 2.0 GHz processor, and a Nvidia Quadro FX 3800 video card.

Figure 2:
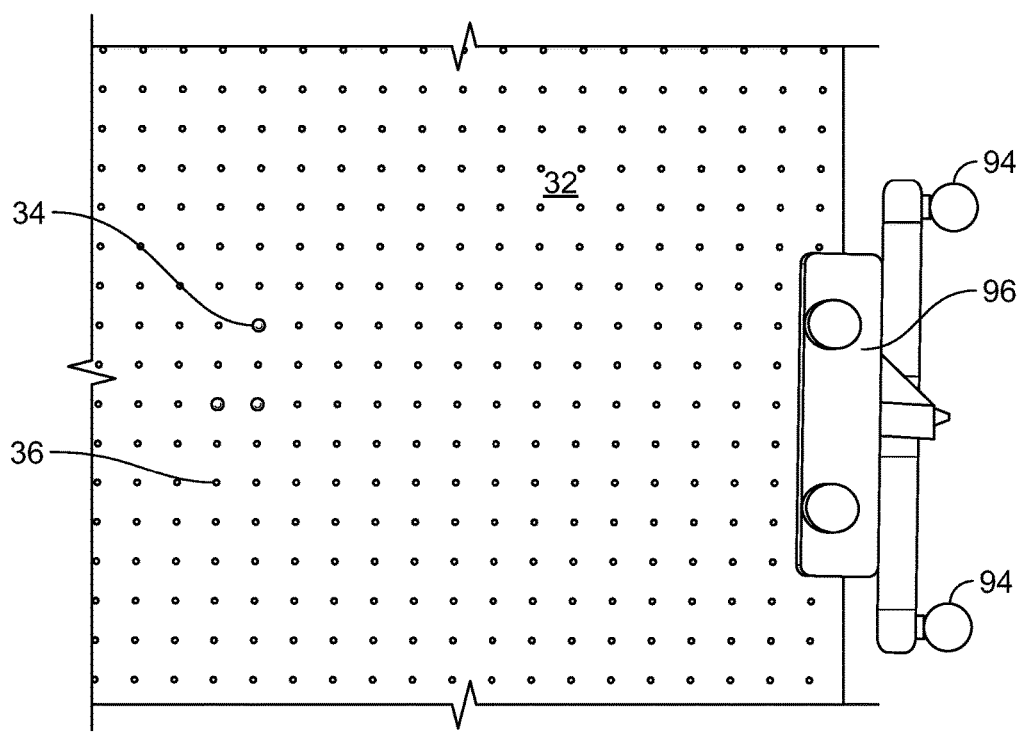
FIGS. 2-4 are various partial views of a calibration assembly including a calibration device, a plate tool, and a mount joining the plate tool to the calibration device.
Figure 3:
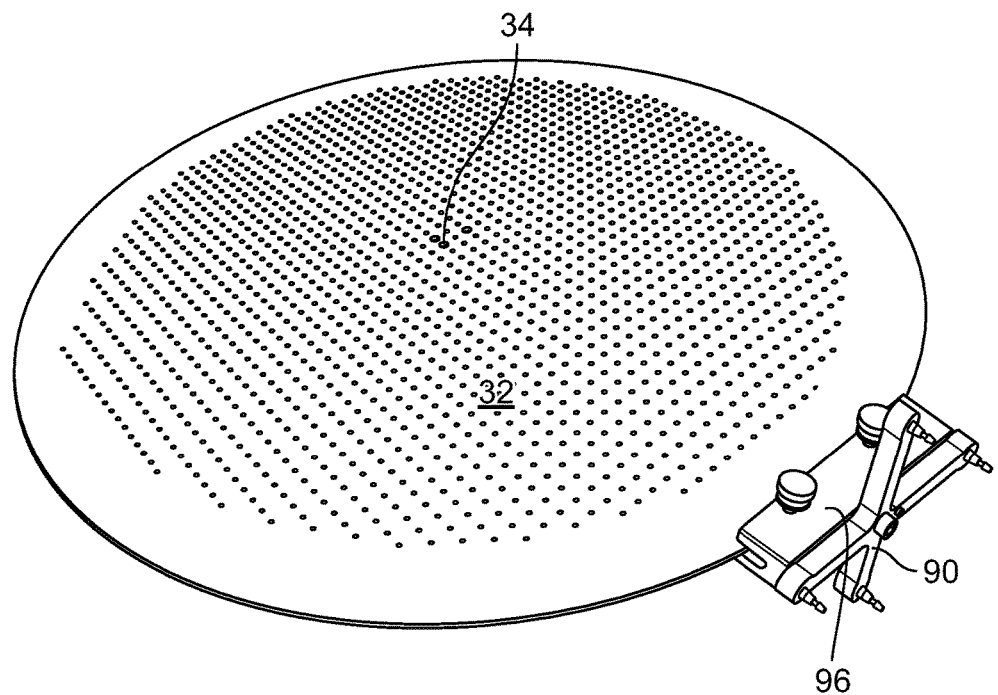
Figure 4:
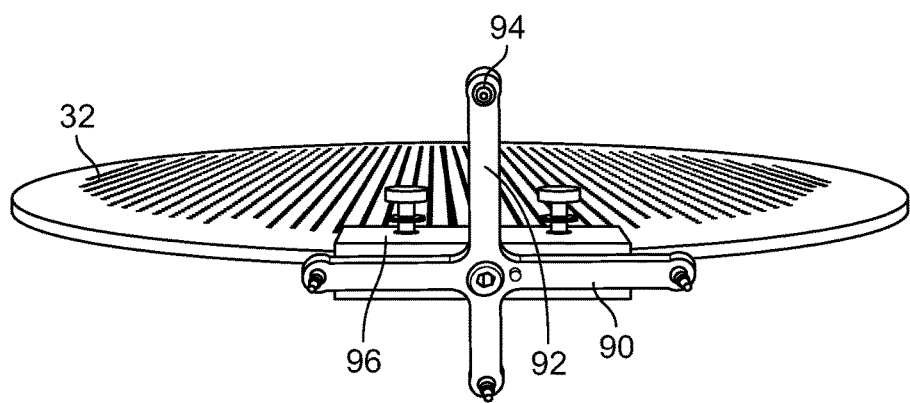

The calibration device 32 may vary widely. In one embodiment of the invention the calibration device is in the form of a plate 32. The plate 32 shown in FIGS. 2-4 is a circular and planar sheet. The plate may be fabricated from metal or plastic. It may have a number of features such as, for example, beads 34 or holes 36 arranged in a grid-like pattern. An example of a calibration device is a plastic plate including a plurality of metal beads 34. Three beads, for example, are positioned on the plate with unequal distances between them and used as a reference marker(s).

A method in accordance with the present invention may be carried out using the system 10 shown in FIG. 1.

A "fluoro tool" or mark 46 is attached to the fluoroscope's image intensifier 42 which can be tracked by the tracking device. The mark may be in the form of a cross having legs of different lengths. The pose of the fluoro tool may thus be obtained.

A calibration device is then placed in the fluoroscopic field of view. Images are obtained of the calibration device 32 at different positions, preferably at multiple angles and orientations.

FIGS. 1-4 show a plate tool 90 attached to the calibration plate 32 whose 3D position and orientation (pose) can be tracked using a tracker device 44. For example, the tracker device may be an infrared or depth sensing camera such as the NDI Polaris tracker manufactured by NDI in Waterloo, Ontario, Canada. The tracking device 44 may be positioned on any fixed surface including the floor, wall, ceiling, or a table. Although the tracking sensor shown in this embodiment is optically based, other techniques (for example, electromagnetic) to track the camera may be employed and are in accordance with the present invention.

The plate tool 90 shown in FIGS. 1-4 comprises a plurality of arms 92, and infrared visible markers 94. Four arms 92 are shown in FIG. 3 and each arm preferably has a different length. However, the invention is not so limited and a different number of arms and lengths may be provided.

The plate tool 90 is preferably rigidly attached to the calibration plate 32. With reference to FIGS. 2-4, the plate tool 90 is shown mounted or associated with the calibration device 32 via fixture or mount 96. The distance between the plate tool and the calibration device 32 is fixed. In another embodiment the plate tool and calibration plate are integral with one another.

The position of the plate tool is obtained from the tracker, and the position of the plate tool relative to the calibration plate may be measured. With this information the grid poses of the calibration plate may be estimated.

Distortion Estimation.

Images obtained from one fluoroscopy projection are received by the processor in computer 50. These images are used to estimate distortion (A, B), pixels per mm in x and y direction (dx, dy), and 2D rotation (theta) and translation (tx, ty) of the calibration device 32 (e.g., a calibration plate) with respect to the fluoroscopic image coordinate system. A and B are polynomial distortion coefficients of order N. There are multiple solutions to the problem if we do not normalize A and B before estimation. For example, note that A and B can introduce scaling, rotation, and translation independently of dx, theta, tx, and ty. To avoid this, the distortion at the center of the fluoroscopic image mask is set to zero with respect to scaling, rotation, and translation. This leads to a unique solution. This normalization is only done for Anterior Posterior (AP) orientation. The values for dx, dy, theta, tx, and ty remain the same for other orientations. Use of multiple images for each orientation combined with normalization, ensures dense sampling of distortion field (estimation of A and B) and preserve uniqueness.

Pose Estimation

The parameters, dx, dy, theta, tx, and ty also give the pose of fluoro tool 46 with respect to the image coordinate system. This is desired for continuously tracking the position of fluoroscopy device 42. These images are processed to estimate focal length (F) and camera center (Cx, Cy) in mm for each orientation.

Estimation of the parameters is done by detecting the grid points in images. Since the pose of the grid points is known relative to the fluoroscope image coordinate system via the tracker, we know the 3D position of the calibration plate 32 as described above. Given the 3D position of the plate and its associated 2D images, we can estimate the calibration parameters, including but not limited to the following: distortion, 2D rotation and translation, focal length, and camera center parameters of the fluoroscopy device at one or more positions.

One example of fluoroscopic device calibration method is described in L. Rai reference (9) listed below. A fluoroscopic device consists of a X-ray source at one end and an image intensifier (XRII) at the other end. The source projects a three-dimensional world point on to XRII to generate a fluoroscopic image. The projected point gets converted to pixel coordinates and undergoes sigmoid and radial distortion. Let (X; Y; Z) be the world point in source's coordinate system and (xd; yd) be the corresponding pixel location in fluoroscopic image. Then $$U(x_d, y_d) = \begin{bmatrix} x_u \\ y_u \end{bmatrix} = \begin{bmatrix} dx\left(f\frac{X}{Z} + cx\right) \\ dy\left(f\frac{Y}{Z} + cy\right) \end{bmatrix} \quad \text{Equation 1}$$

where U is the undistortion function, (dx; dy) are pixel/mm values for XRII, f is the focal length in mm, and (cx; cy) is the camera center in mm U is typically modeled as a polynomial of order Nd.

A goal of calibration is to estimate U, (dx; dy), f, and (cx; cy). These are known as, for example, intrinsic parameters. Except for (dx; dy), the rest of the calibration parameters, vary with the C-arm orientation. This example employs a NDI Polaris tracker unit to track XRII and a calibration plate as shown in FIG. 1. The C-arm and the calibration plate are attached with fluoroTool and plateTool, respectively, which can be tracked in real-time. The method estimates the pose of fluoroTool with respect to the source, $M_{fluoroTool}$, in addition to the intrinsic parameters. (dx; dy), U, and $M_{fluoroTool}$ are estimated first by attaching the calibration plate to the XRII imaging plane and acquiring fluoroscopic images. Let $(x_p; y_p)$ be the coordinates of a metal bead in mm and $(x_d; y_d)$ be the corresponding pixel location. Then $$U(x_d, y_d) = \begin{bmatrix} dx & 0 \\ 0 & dy \end{bmatrix} T(x_p, y_p) \quad \text{Equation 2}$$

where T is a 2D transformation between the plate and XRII coordinate system.

The unknowns can be estimated by solving this equation for all visible metal beads. U can be known up to an unknown 2D scaling, rotation, and translation. To ensure consistent estimation (independent of how the plate is attached), coefficients of U for zero C-arm orientation (AP view) are normalized such that the distortion at the image-center has zero scaling, rotation, and translation. Since, (dx; dy) and T are independent of the C-arm orientation, they are used to estimate U for other C-arm orientations. Normalization to U is not applied for these views. The plate is rotated in 2D and multiple such images are acquired per fluoroscopic device orientation for dense estimation of U. Estimation of T gives $M_{fluoroTool}$ as well.

The next step is to estimate f; cx; and cy for a given C-arm orientation. This is done by placing the plate in between the fluoroscopic X-RAY source and XRII and acquiring one or more images. Use of tracker and knowledge of $M_{fluoroTool}$ gives 3D locations (X; Y; Z) of metal beads in source's coordinate system. Via Equation (1), the pixel locations of metal beads generate a linear system of equations giving f; cx; and cy. This step is repeated for other C-arm orientations as well.

Once the calibration parameters are estimated, the operator may adjust the received fluoro 2D projection images accordingly to make the fluoro images more accurate and to compensate for the distortion of each individual fluoroscope.

Other modifications and variations can be made to the disclosed embodiments without departing from the subject invention.

REFERENCES

1. W. E. Higgins, S. A. Merritt, and L. Rai, "Guidance method based on 3D-2D pose estimation and 3D-CT registration with application to live bronchoscopy", U.S. Pat. No. 7,756,563 B2.
2. Z. Zhang, "Flexible camera calibration by viewing a plane from unknown orientations", ICCV 1999, pages 666-673.
3. J. Heikkila and O. Silven, "A four-step camera calibration procedure with implicit image correction", CVPR 1997, pages 1106-1112.
4. T. Leloup, W. El Kazzi, O. Debeir, F. Schuind, and N. Warzee, "Automatic fluoroscopic Image Calibration for traumatology intervention guidance", Eurocon 2005, pages 374-377.

5. L. F. Gutierrez, C. Ozturk, E. R. McVeigh, and R. J. Lederman, "A practical global distortion correction method for an image intensifier based x-ray fluoroscopy system" Medical Physics March 2008, 35(3), pages 997-1007.
6. W. E. Higgins, S. A. Merritt, and L. Rai, "Fast 3D-2D image registration method with application to continuously guided endoscopy", U.S. Pat. No. 7,756,563 B2.
7. D. A. Forsyth and Jean Ponce, "Computer Vision: A modern approach", Prentice Hall Professional Technical Reference, 2002.
8. R. Fahrig, M. Moreau, and D. W. Holdsworth, "Three-dimensional computed tomographic reconstruction using a C-arm mounted XRII: Correction of image intensifier distortion", Med. Phys. 24(7): 1097-1106, July 1997.
9. L. Rai, J. Gibbs, and H. Wibowo, "A C-arm calibration method with application to fluoroscopic image-guided procedures", Medical Imaging 2012: Image-Guided Procedures, Robotic Interventions, and Modeling. Edited by Holmes, David R., III; Wong, Kenneth H. Proceedings of the SPIE, Volume 8316, pp. 831625-831625-11 (2012).

We claim:

1. A method for determining calibration parameters of a medical imaging device, said method comprising the steps of:
    a) providing a calibration device comprising at least one reference marker visible under x-ray;
    b) determining the pose of the calibration device with a tracking device and a plate tool rigidly connected to the calibration device, said plate tool being sensed by said tracking device;
    c) receiving a 2D image of calibration device using the imaging device; and
    d) calculating at least one calibration parameter of the imaging device based on image information from said 2D image and said pose.

2. The method of claim 1 wherein said pose of the imaging device is a fluoroscopic device and is based on sensing a pose of the fluoroscopic device with said tracking device.

3. The method of claim 2 wherein the imaging device is a fluoroscopic device and at least on calibration parameters are selected from the group consisting of dx, dy, theta, tx, ty, focal length, and distortion.

4. The method of claim 3 wherein the plate tool comprises a plurality of arms each having a different length.

5. The method of claim 4 wherein the calibration device is a planar circular shaped plastic plate.

6. The method of claim 5 wherein the reference markers of the calibration plate are a plurality of metal beads.

7. A system for calibrating a medical imaging device comprises:
    a processor;
    a calibration device having at least one reference marker visible under x-ray; and
    a plate tool in fixed engagement with the calibration device and comprising at least one locator visible with a tracking device, and wherein the processor is operable to:
    calculate a pose of said reference marker based on said position of the calibration device and the pose of the imaging device;
    receive a 2D image of the calibration device using the medical imaging device; and
    calculate at least one calibration parameter of imaging device based on image information from said 2D image and said pose of said reference marker.

8. The system of claim 7 wherein the processor is operable to calculate at least one calibration parameters selected from the group consisting of dx, dy, theta, tx, ty, focal length, and distortion.

9. The system of claim 7 wherein the plate tool comprises a plurality of arms each having a different length.

10. The system of claim 7 wherein the calibration device is a planar circular shape.

11. The system of claim 10 wherein the calibration device comprises a plastic plate.

12. The system of claim 11 wherein the at least one reference marker comprises a plurality of metal beads.

13. A calibration assembly comprising a calibration plate defining a first plane, a plurality of fixed reference markers visible under a fluoroscope or x-ray device arranged on the calibration plate, a plate tool in a known rigidly fixed engagement to said calibration plate, and at least one locator arranged on the plate tool, and wherein arms of the plate tool define a second plane, and the plate tool and calibration plate are arranged such that the first plane is perpendicular to the second plane.

14. The calibration assembly of claim 13 wherein said calibration plate is comprised of polymer and said reference markers include at least three metal beads.

15. The calibration assembly of claim 13 wherein said plate tool is in the shape of a cross comprising at least four arms, each having a different length.

16. The calibration assembly of claim 13 wherein the locators are infrared visible.

17. The calibration assembly of claim 13 further comprising a fixture, and wherein the plate tool is mounted to the calibration plate via a fixture.

18. The calibration assembly of claim 17 wherein calibration plate is planar.

* * * * *